United States Patent
Arsenjans et al.

(10) Patent No.: US 12,060,368 B2
(45) Date of Patent: Aug. 13, 2024

(54) SELENOPHENOCHROMENE HYDROXAMIC ACIDS, PREPARATION AND USE AS ANGIOGENESIS INHIBITORS

(71) Applicant: Latvian Institute of Organic Synthesis, Riga (LV)

(72) Inventors: Pavels Arsenjans, Riga (LV); Jelena Vasiljeva, Riga (LV); Ilona Domraceva, Riga (LV)

(73) Assignee: Latvian Institute of Organic Synthesis, Riga (LV)

( * ) Notice: Subject to any disclaimer, the term of this patent is extended or adjusted under 35 U.S.C. 154(b) by 729 days.

(21) Appl. No.: 17/270,588

(22) PCT Filed: Dec. 18, 2018

(86) PCT No.: PCT/IB2018/060224
§ 371 (c)(1),
(2) Date: Feb. 23, 2021

(87) PCT Pub. No.: WO2020/053639
PCT Pub. Date: Mar. 19, 2020

(65) Prior Publication Data
US 2021/0403486 A1    Dec. 30, 2021

(30) Foreign Application Priority Data
Sep. 13, 2018   (LV) .................................. P-18-72

(51) Int. Cl.
*C07D 517/04*    (2006.01)
*A61P 35/00*    (2006.01)

(52) U.S. Cl.
CPC ............ *C07D 517/04* (2013.01); *A61P 35/00* (2018.01)

(58) Field of Classification Search
CPC ....................................................... A61P 35/00
See application file for complete search history.

(56) References Cited

U.S. PATENT DOCUMENTS

| 5,427,779 A * | 6/1995 | Elsner ................. G01N 33/545 424/490 |
| 10,561,681 B2 * | 2/2020 | Arsenjans ............ C07D 517/04 |
| 2023/0002411 A1 * | 1/2023 | Arsenjans .............. A61K 45/06 |

FOREIGN PATENT DOCUMENTS

WO    WO 2018/015788    1/2018

OTHER PUBLICATIONS

Arsenyan et al., "Selenopheno[3,2-c]- and [2,3-c]coumarins: Synthesis, cytotoxicity, angiogenesis inhibition, and antioxidant properties," Comptes Rendus Chimie, Apr. 2015, 18(4):399-409.
Justilien et al., "Matrix metalloproteinase-10 is required for lung cancer stem cell maintenance, tumor initiation and metastatic potential," PLoS One, 2012, 7(4):e35040, 12 pages.
Pal et al., "Hydroxamic acid—A novel molecule for anticancer therapy," J Adv Pharm Technol Res, Apr. 2012, 3(2):92-9.
PCT International Search Report and Written Opinion in International Appln. No. PCT/IB2018/060224, dated Feb. 1, 2019, 8 pages.
Reiter et al., "Pyran-containing sulfonamide hydroxamic acids: potent MMP inhibitors that spare MMP-1," Bioorg Med Chem Lett, Jul. 2004, 14(13):3389-95.
Tommasi et al., "Potent and selective 2-naphthylsulfonamide substituted hydroxamic acid inhibitors of matrix metalloproteinase-13," Bioorg Med Chem Lett, Nov. 2011, 21(21):6440-5.
Wang et al., "Mutagenicity and antibacterial activity of hydroxamic acids," Antimicrob Agents Chemother, Apr. 1977, 11(4):753-5.

* cited by examiner

*Primary Examiner* — John S Kenyon
*Assistant Examiner* — Gillian A Hutter
(74) *Attorney, Agent, or Firm* — Fish & Richardson P.C.

(57) ABSTRACT

The present invention relates to a novel selenophenochromene hydroxamic acids as angiogenesis inhibitors, as well as methods of their manufacturing and use in different pharmaceutical compositions for the treatment or prevention of various diseases and disorders by administration of such substances.

22 Claims, No Drawings
Specification includes a Sequence Listing.

SEQUENCE LISTING

<160> NUMBER OF SEQ ID NOS: 1

<210> SEQ ID NO 1
<211> LENGTH: 26
<212> TYPE: PRT
<213> ORGANISM: Artificial Sequence
<220> FEATURE:
<223> OTHER INFORMATION: OmniMMPTM fluorogenic substrate
    Mca-Pro-Leu-Gly-Leu-Dpa-Ala-Arg-NH2 was mentioned in the
    procedure for the detection of MMP activity as standard sensitive
    fluorogenic substrate for most matrix metalloproteinase (MMP)
    enzymes.
<300> PUBLICATION INFORMATION:
<301> AUTHORS: Neumann, Kubota, Frei, Ganu, Leppert
<302> TITLE: Characterization of Mca-Lys-Pro-Leu-Gly-Dpa-Ala-Arg-NH2, a
    fluorogenic substrate with increased specificity constants for
    collagenases and tumor necrosis factor converting enzyme
<303> JOURNAL: Anal Biochem
<304> VOLUME: 328
<305> ISSUE: 2
<306> PAGES: 166-73
<307> DATE: 2004-05-15

<400> SEQUENCE: 1

Met Cys Ala Leu Tyr Ser Pro Arg Leu Glu Gly Leu Tyr Leu Glu Asp
1               5                   10                  15

Pro Ala Ala Leu Ala Ala Arg Gly Asn His
            20                  25

SELENOPHENOCHROMENE HYDROXAMIC ACIDS, PREPARATION AND USE AS ANGIOGENESIS INHIBITORS

CROSS REFERENCE TO RELATED APPLICATIONS

This application is a U.S. national phase filing under 35 U.S.C. § 371 of International Application No. PCT/IB2018/060224, filed Dec. 18, 2018, which claims priority of Latvian Application No. P-18-72, filed Sep. 13, 2018. The International Application was published in English on Mar. 19, 2020 as WO 2020/053639 under PCT Article 21(2). The entire contents of the prior applications are incorporated herein by reference in their entirety.

FIELD OF THE INVENTION

The present invention relates to a novel selenophenochromenone hydroxamic acids, which may act as angiogenesis inhibitors, methods for their synthesis and the treatment and/or prevention of various diseases and disorders by administration of such substances.

SEQUENCE LISTING

This application contains a Sequence Listing that has been submitted electronically as ASCII text file named (SEQLIST.TXT). The ASCII text file, created on May 13, 2021 is 1.28 kilobytes in size. The material in the ASCII text file is hereby incorporated by reference in its entirety.

BACKGROUND OF THE INVENTION

Cancers are major cause of mortality of all ages. Tumor growth is a complex multistage process. Occurrence and progressive tumor growth is dependent on both the properties of cancer cells, and the state of immunological reactivity. This determines the diversity of approaches of the cancer therapy using one or several basic methods: surgery, radiotherapy, chemotherapy and immunotherapy. Their goal is to minimize the mass of the tumor. Matrix metalloproteinases (MMPs) stimulate tumor invasion and metastasis by degrading the extracellular matrix. Notably, small molecules with hydroxamic acid moieties are potent not only in the field of cancer therapy, but also as agents preventing mutagenicity [*J Adv Pharm Technol Res*. 2012, 3, 92-99].

Among the various derivatives of hydroxamic acid, SAHA (Suberoylanilide Hydroxamic Acid) is considered as a potent anticancer agent for the treatment of cutaneous manifestations in patients with cutaneous T cell lymphoma (CTCL). Besides, various hydroxamic acids were approved as medicaments in therapy of cancers. For example, Batimastat is an anticancer drug that belongs to the family of drugs called angiogenesis inhibitors; Ilomastat exhibit a broad-spectrum matrix metalloproteinase inhibitor as well as Marimastat, which was proposed as antineoplastic drug. Also, salicylhydroxamic acid has shown antitubercular activity both in vivo and in vitro [*Antimicrob Agents Chemother.* 1977, 11, 753-5]. It was found that sterically hindered sulfonamide hydroxamic acids exhibit ability to suppress MMP-1 and MMP-13 activity. The metabolically more stable compounds in the series contain either a monocyclic or bicyclic pyran ring adjacent to the hydroxamate group [*Bioorg Med Chem Lett.*, 2004, 14, 3389-3395; *Bioorg Med Chem Lett.* 2011, 21, 6440-6445]. Besides, overexpression of MMP10 (stromelysin 2) increases development of lung cancer stem-like cells (CSC) [*PLoS One*, 2012, 7, e35040].

Recently we claimed 2H-selenopheno[3,2-h]chromenes as antimetastatic agents in treatment of carcinomas and melanoma. These derivatives exhibit low acute toxicity and almost completely (98%) prevent mammary carcinoma 4T1 metastasis formation in vivo (BALB/c female mice) and melanoma B16-F10 metastasis in lung by 82% without any visual side effects [WO2018015788 (A1)].

Unfortunately, the number of cancer diagnosis in past few years has increased almost twice. In clinical practice, the treatment of cancer involves a wide range of chemotherapy drugs. Besides, most of them exhibit various side effects, high toxicity and moderate selectivity. Therefore, a new generation of selective, low toxic anticancer agent is one of the main tasks in medicinal chemistry and pharmaceutical industries.

The Present Invention

We have determined that certain selenophenochromene hydroxamic acids exhibit ability suppresses matrix metalloproteinases and therefore may act as inhibitors of angiogenesis. Therefore, these substances may be therapeutically beneficial in the treatment of conditions which involve treatment and/or prevention of various diseases and disorders including cell proliferation. These substances may be administered in the form of a pharmaceutical composition, wherein they are present together with one or more pharmaceutically acceptable diluents, carriers, or excipients.

OBJECTS OF THE INVENTION

It is an object of the present invention to provide novel pharmaceutical compounds, which are inhibitors of matrix metalloproteinases and therefore can be used as angiogenesis inhibitors, methods for their synthesis and the treatment and/or prevention of various diseases and disorders caused by overexpression of matrix metalloproteinases by administration of such substances.

SUMMARY OF THE INVENTION

We disclosed compounds selected from those of Formula I

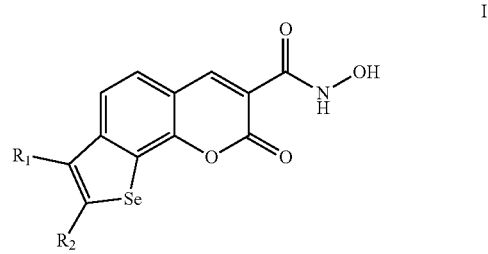

$R_1$ represents a halogen atom (e.g. Br); and $R_2$ represents $C_{1-4}$-alkyl-N-heterocyclyl.

As used herein, the term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms. The term "alkylene" refers to a divalent alkyl, e.g., —CH$_2$—, —CH$_2$CH$_2$—, —CH$_2$CH$_2$CH$_2$— or —CH$_2$CH(CH$_3$)CH$_2$—. An alkyl or alkylene may be optionally substituted.

The term "cycloalkyl" as used herein refers to nonaromatic, saturated or partially unsaturated cyclic, bicyclic, tricyclic or polycyclic hydrocarbon groups having 3 to 12 carbons. Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkenylene" refers to a divalent alkenyl, e.g., —CH=CH—, —CH=CH$_2$CH$_2$— or —CH=C=CH—.

The term "heterocyclyl" as used herein refers to a nonaromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

As used herein, the term "halogen" refers to fluorine, chlorine, bromine and iodine.

Embodiments of the present disclosure encompass any racemic, optically-active, polymorphic, tautomeric, or stereoisomeric form or mixture thereof, of a compound of the disclosure, which possesses the useful properties described herein.

In cases where compounds are sufficiently basic or acidic to form stable nontoxic acid or base salts, use of the compounds as pharmaceutically acceptable salts may be appropriate. Examples of pharmaceutically acceptable salts within the scope of embodiments of the present disclosure include organic acid addition salts formed with acids which form a physiological acceptable anion and inorganic salts.

Specific compounds of Formula I within the present invention include but are not limited to:

7-Bromo-N-hydroxy-8-((4-methylpiperazin-1-yl)methyl)-2-oxo-2H-selenopheno[3,2-h]chromene-3-carboxamide 7-Bromo-N-hydroxy-2-oxo-8-(piperazin-1-ylmethyl)-2H-selenopheno[3,2-h]chromene-3-carboxamide 7-Bromo-N-hydroxy-2-oxo-8-(2-(piperazin-1-yl)ethyl)-2H-selenopheno[3,2-h]chromene-3-carboxamide 8-((1,4-Diazepan-1-yl)methyl)-7-bromo-N-hydroxy-2-oxo-2H-selenopheno[3,2-h]chromene-3-carboxamide

DETAILED DESCRIPTION OF THE INVENTION

As used herein, the term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms. The term "alkylene" refers to a divalent alkyl, e.g., —CH$_2$—, —CH$_2$CH$_2$—, —CH$_2$CH$_2$CH$_2$— or —CH$_2$CH(CH$_3$)CH$_2$—. An alkyl or alkylene may be optionally substituted.

The term "cycloalkyl" as used herein refers to nonaromatic, saturated or partially unsaturated cyclic, bicyclic, tricyclic or polycyclic hydrocarbon groups having 3 to 12 carbons. Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkenylene" refers to a divalent alkenyl, e.g., —CH=CH—, —CH=CH$_2$CH$_2$— or —CH=C=CH—.

The term "heterocyclyl" as used herein refers to a nonaromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

As used herein, the term "halogen" refers to fluorine, chlorine, bromine and iodine.

Embodiments of the present disclosure encompass any racemic, optically-active, polymorphic, tautomeric, or stereoisomeric form or mixture thereof, of a compound of the disclosure, which possesses the useful properties described herein.

In cases where compounds are sufficiently basic or acidic to form stable nontoxic acid or base salts, use of the compounds as pharmaceutically acceptable salts may be appropriate. Examples of pharmaceutically acceptable salts within the scope of embodiments of the present disclosure include organic acid addition salts formed with acids which form a physiological acceptable anion and inorganic salts.

Scheme 1 describes the preparation of compounds of Formula I of the present invention. All the starting materials 1-4 are prepared by procedures described in WO2018015788 (A1), intermediates 5-8—by procedures well known to one of ordinary skill in organic chemistry. All the final compounds of the present invention are prepared by procedures described in these charts or by procedures analogous thereto, which procedures would be well known to one of ordinary skill in organic chemistry. All the variables used in the schemes are as defined below or as in the claims.

Scheme 1. General procedure toward compounds of Formula I.

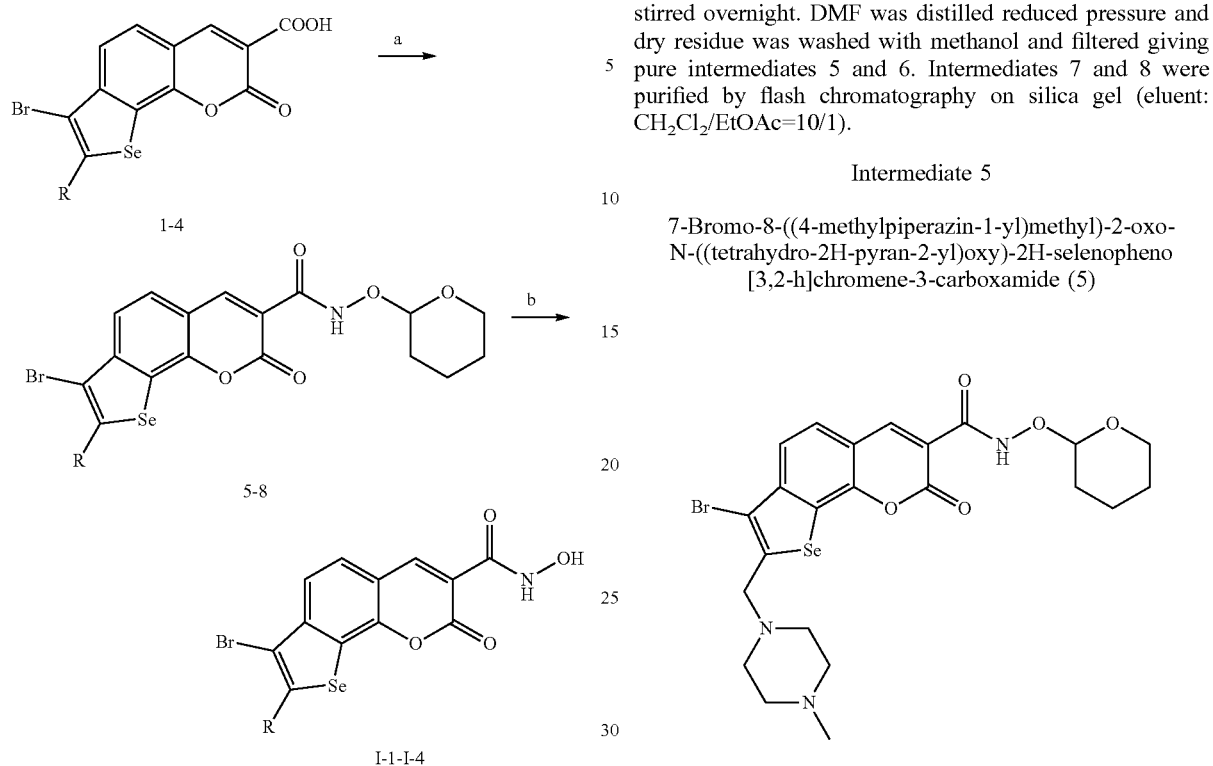

Reaction conditions:
a: THP—ONH₂, HOBt, EDC × HCl, NMM, DMF;
b: HCl(Et₂O), DCM

We have found that the treatment of selenophenochromenone carboxylic acids 1-4 with O-(tetrahydro-2H-pyran-2-yl)hydroxylamine in the presence of 1-hydroxybenzotriazole and (0.8 mmol, 122 mg) and N-(3-dimethylaminopropyl)-NV-ethylcarbodiimide hydrochloride, N-methyl morpholine in DMF led to the formation of intermediates 5-8 in 62-76% yields. Next, THP and Boc protecting groups were removed using hydrogen chloride solution in diethyl ether/DCM mixture. Surprisingly, desired hydroxamic acids I-1-I-4 were isolated as hydrochlorides by a simple filtration in very high yields without any additional purification.

EXAMPLES

Preparation of the disclosed compounds of the present invention is described in the following examples, which are intended as an illustration of and not a limitation upon the scope of the invention.

Hereinafter, "DMF" is defined as N,N-dimethylformamide, "DMSO" as dimethyl sulfoxide, "HCl" as hydrochloric acid, "MeCN" as acetonitrile, "DIEA" as diisopropylethylamine, "EtOAc" as ethyl acetate, "rt" as room temperature.

General procedure for the preparation of 7-bromo-8-(substituted)-2-oxo-N-((tetrahydro-2H-pyran-2-yl)oxy)-2H-selenopheno[3,2-h]chromene-3-carboxamides (5-8): A vial charged with 1-4 (0.5 mmol), 1-hydroxybenzotriazole (0.8 mmol, 122 mg) and O-(tetrahydro-2H-pyran-2-yl)hydroxylamine (0.8 mmol, 94 mg) were dissolved in DMF (10 mL). Then N-methyl-morpholine (1.3 mmol, 142 μL) and N-(3-dimethylaminopropyl)-N'-ethylcarbodiimide hydrochloride (1 mmol, 192 mg) were added and reaction mixture was stirred overnight. DMF was distilled reduced pressure and dry residue was washed with methanol and filtered giving pure intermediates 5 and 6. Intermediates 7 and 8 were purified by flash chromatography on silica gel (eluent: CH₂Cl₂/EtOAc=10/1).

Intermediate 5

7-Bromo-8-((4-methylpiperazin-1-yl)methyl)-2-oxo-N-((tetrahydro-2H-pyran-2-yl)oxy)-2H-selenopheno[3,2-h]chromene-3-carboxamide (5)

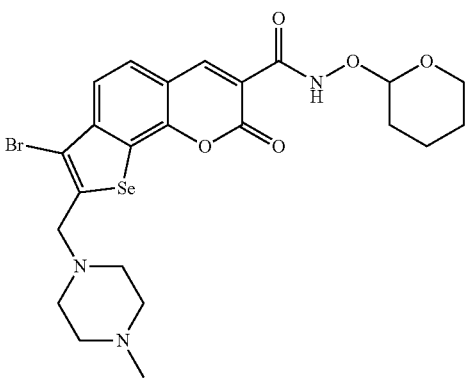 [SMILES: CN1CCN(Cc2[se]c3c(ccc4cc(C(=O)NOC5CCCCO5)c(=O)oc43)c2Br)CC1]

Yield, 76%. $^1$H-NMR (CDCl₃): 1.62-1.98 (m, 6H), 2.51 (s, 3H, CH₃), 2.65-2.89 (m, 8H), 3.69-3.73 (m, 1H), 3.92 (s, 2H, NCH₂), 4.06-4.12 (m, 1H), 5.13-5.15 (m, 1H), 7.68 (d, 1H), 7.77 (d, 1H), 9.00 (s, 1H), 11.05 (s, 1H). $^{13}$C-NMR (CDCl₃): 18.3, 24.9, 27.9, 45.2, 52.1, 54.8, 58.5, 62.4, 102.3, 113.9, 116.6, 121.7, 125.5, 126.3, 146.4, 149.3, 151.7, 159.2, 160.3. LC-MS [M+1]: 584.

Intermediate 6

Tert-butyl 4-((7-bromo-2-oxo-3-(((tetrahydro-2H-pyran-2-yl)oxy)carbamoyl)-2H-selenopheno[3,2-h]chromen-8-yl)methyl)piperazine-1-carboxylate (6)

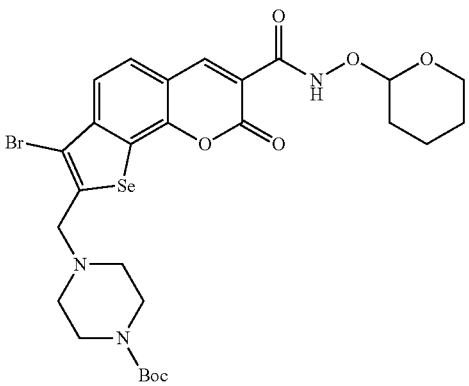 [SMILES: CC(C)(C)OC(=O)N1CCN(Cc2[se]c3c(ccc4cc(C(=O)NOC5CCCCO5)c(=O)oc43)c2Br)CC1]

Yield, 64%. $^1$H-NMR (CDCl₃): 1.46 (s, 9H), 1.60-1.96 (m, 6H), 2.61-2.63 (m, 4H), 3.47-3.49 (m, 4H), 3.67-3.72 (m, 1H), 3.85 (s, 2H), 4.05-4.11 (m, 1H), 5.12-5.14 (m, 1H), 7.61 (d, 1H), 7.70 (d, 1H), 8.93 (s, 1H), 11.04 (s, 1H).

¹³C-NMR (CDCl₃): 18.3, 24.9, 27.9, 28.3, 53.4, 58.8, 62.3, 79.8, 102.2, 106.0, 113.8, 116.5, 121.4, 125.4, 126.2, 146.3, 149.1, 151.6, 152.4, 154.6, 159.1, 160.1. LC-MS [M+1]: 670.

Intermediate 7

Tert-butyl 4-(2-(7-bromo-2-oxo-3-(((tetrahydro-2H-pyran-2-yl)oxy)carbamoyl)-2H-selenopheno[3,2-h]chromen-8-yl)ethyl)piperazine-1-carboxylate (7)

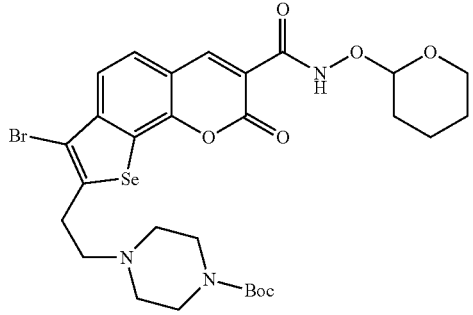 [SMILES: CC(C)(C)OC(=O)N1CCN(CCc2[se]c3c(ccc4cc(C(=O)NOC5CCCCO5)c(=O)oc43)c2Br)CC1]

Yield, 69%. ¹H-NMR (CDCl₃): 1.48 (s, 9H), 1.60-1.95 (m, 6H), 2.54-2.59 (m, 4H), 2.69 (t, 2H), 3.17 (t, 2H), 3.58-3.62 (m, 4H), 3.68-3.71 (m, 1H), 4.05-4.11 (m, 1H), 5.12-5.14 (m, 1H), 7.55 (d, 1H), 7.69 (d, 1H), 8.87 (s, 1H), 11.05 (s, 1H). ¹³C-NMR (CDCl₃): 18.3, 24.9, 27.9, 28.4, 29.6, 52.5, 56.0, 62.3, 79.7, 102.2, 108.5, 113.6, 115.9, 121.5, 125.4, 126.0, 127.5, 144.7, 148.1, 149.1, 151.5, 154.7, 159.2, 160.4. LC-MS [M+1]: 684.

Intermediate 8

Tert-butyl 4-((7-bromo-2-oxo-3-(((tetrahydro-2H-pyran-2-yl)oxy)carbamoyl)-2H-selenopheno[3,2-h]chromen-8-yl)methyl)-1,4-diazepane-1-carboxylate (8)

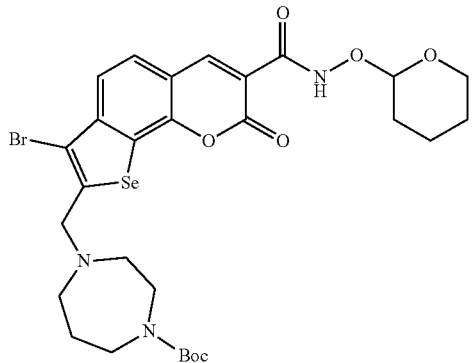 [SMILES: CC(C)(C)OC(=O)N1CCCN(Cc2[se]c3c(ccc4cc(C(=O)NOC5CCCCO5)c(=O)oc43)c2Br)CC1]

Yield, 62%. ¹H-NMR (CDCl₃): 1.48 (s, 9H), 1.61-1.97 (m, 6H), 2.78-2.89 (m, 4H), 3.48-3.56 (m, 4H), 3.69-3.72 (m, 1H), 3.96 (s, 2H), 4.06-4.12 (m, 1H), 5.13-5.15 (m, 1H), 7.65 (d, 1H), 7.73 (d, 1H), 8.97 (s, 1H), 11.06 (s, 1H). LC-MS [M+1]: 684.

General procedure for the preparation of 8-(substituted)-7-bromo-N-hydroxy-2-oxo-2H-selenopheno[3,2-h]chromene-3-carboxamides (I-1-I-4): To a stirred solution of carboxamide (5-8) (150-200 mg) in dichloromethane (15 mL) 1N hydrogen chloride solution in diethyl ether (5 mL) was added dropwise. Reaction mixture was stirred overnight or till the consumption of the starting material. The precipitates were filtered off and dried, giving pure compound (I-1-I-4).

Example 1

7-Bromo-N-hydroxy-8-((4-methylpiperazin-1-yl)methyl)-2-oxo-2H-selenopheno[3,2-h]chromene-3-carboxamide hydrochloride (I-1)

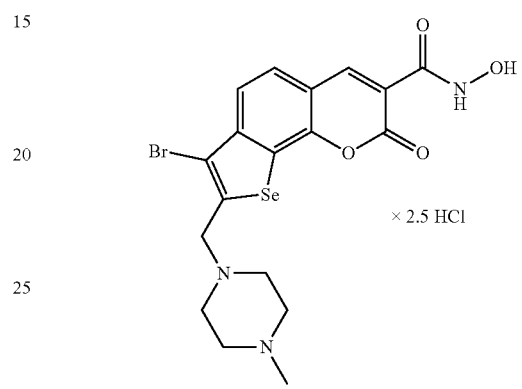

Yield, 84%, m.p.>200° C. ¹H-NMR (D₂O): 2.99 (s, 3H), 3.15-3.76 (m, 8H), 4.08 (s, 2H), 7.18-7.20 (m, 2H), 8.09 (s, 1H). LC-MS [M+1]: 500. HRMS (ESI): C₁₈H₁₈BrN₃O₄Se, calcd. [M+1]: 499.9646, found: 499.9726. Elemental analysis, calcd. (%) for C₁₈H₁₈BrN₃O₄Se×2.5 HCl: C, 36.62; H, 3.50; N, 7.12; found: C, 36.54; H, 3.63; N, 6.91.

Example 2

7-Bromo-N-hydroxy-2-oxo-8-(piperazin-1-ylmethyl)-2H-selenopheno[3,2-h]chromene-3-carboxamide hydrochloride (I-2)

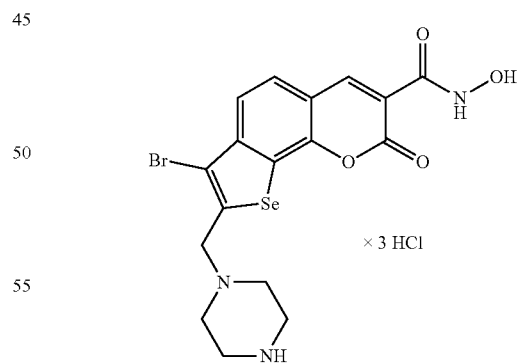

Yield, 99%, m.p.>200° C. ¹H-NMR (DMSO-d₆): 2.90-2.95 (m, 4H), 3.15-3.23 (m, 4H), 4.08 (s, 2H), 7.76 (d, 1H), 8.02 (d, 1H), 8.85 (s, 1H), 9.04 (br s, 2H), 10.82 (br s, 1H). LC-MS [M+1]: 486. HPLC purity: 98.4% (detection: UV 254 nm). HRMS (ESI): C₁₇H₁₆BrN₃O₄Se, calcd. [M+1]: 485.9489, found: 485.9569. Elemental analysis, calcd. (%) for C₁₇H₁₆BrN₃O₄Se×3 HCl: C, 34.34; H, 3.22; N, 7.07; found: C, 34.28; H, 3.39; N, 6.89.

Example 3

7-Bromo-N-hydroxy-2-oxo-8-(2-(piperazin-1-yl)ethyl)-2H-selenopheno[3,2-h]chromene-3-carboxamide hydrochloride (I-3)

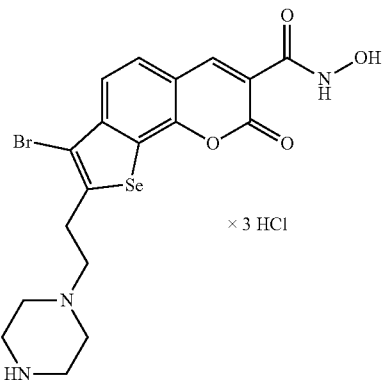 [SMILES: O=C(NO)c1cc2ccc3c(Br)c(CCN4CCNCC4)[se]c3c2oc1=O]

Yield, 99%, m.p.>200° C. $^1$H-NMR (D$_2$O): 3.31-3.34 (m, 4H), 3.46-3.47 (m, 4H), 3.60-3.63 (m, 4H), 7.47-7.48 (m, 2H), 8.36 (s, 1H). LC-MS [M+1]: 500. HPLC purity: 98.3% (detection: UV 254 nm). HRMS (ESI): C$_{18}$H$_{18}$BrN$_3$O$_4$Se, calcd. [M+1]: 499.9646, found: 499.9743. Elemental analysis, calcd. (%) for C$_{18}$H$_{18}$BrN$_3$O$_4$Se×3 HCl: C, 35.52; H, 3.48; N, 6.90; found: C, 35.38; H, 3.35; N, 6.79.

Example 4

8-((1,4-Diazepan-1-yl)methyl)-7-bromo-N-hydroxy-2-oxo-2H-selenopheno[3,2-h]chromene-3-carboxamide hydrochloride (I-4)

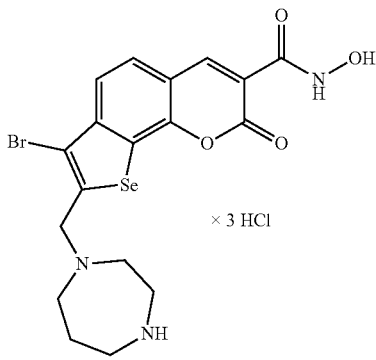 [SMILES: O=C(NO)c1cc2ccc3c(Br)c(CN4CCCNCC4)[se]c3c2oc1=O]

Yield, 94%. $^1$H-NMR (DMSO-d$_6$): 1.94-2.00 (m, 2H), 2.96-2.98 (m, 2H), 3.12-3.14 (m, 2H), 3.20-3.28 (m, 4H), 4.21 (s, 2H), 7.71 (d, 1H), 7.89 (d, 1H), 8.70 (s, 1H). LC-MS [M+1]: 500. HPLC purity: 97.7% (detection: UV 254 nm). HRMS (ESI): C$_{18}$H$_{18}$BrN$_3$O$_4$Se, calcd. [M+1]: 499.9646, found: 499.9730. Elemental analysis, calcd. (%) for C$_{18}$H$_{18}$BrN$_3$O$_4$Se×3 HCl: C, 35.52; H, 3.48; N, 6.90; found: C, 35.37; H, 3.39; N, 6.81.

Angiogenesis Inhibition

Matrix metalloproteinases MMPs, also designated matrixins, hydrolyze components of the extracellular matrix. These proteinases play a central role in many biological processes, such as embryogenesis, normal tissue remodeling, wound healing, and angiogenesis, and in diseases such as atheroma, arthritis, cancer, and tissue ulceration. Cancer invasion and metastasis develops through a series of steps that involve the loss of cell to cell and cell to matrix adhesion, degradation of extracellular matrix and induction of angiogenesis. Matrix metalloproteinase MMP-10 (stromelysin 2) is one of the lesser studied MMPs, is limited to epithelial cells and can facilitate tumor cell invasion by targeting collagen, elastin and laminin. However, it is known that over expression of MMP10 is usually detected for oncological patients especially with cervical, colon, and bladder cancers.

Inhibition of matrix metalloproteinase enzymes by synthesized selenopheno[3,2-h]chromenes I-1-I-4 was detected on MMP Inhibitor Fluorimetric Profiling kit using NNGH (N-isobutyl-N-4-methoxyphenylsulfonyl)glycyl-hydroxamic acid) as a standard.

Surprisingly, novel selenopheno[3,2-h]chromene hydroxamic acid I-1 exhibits ability to selectively inhibit MMP 10 (stromelysin 2) up to 97% in 20 μM concentration (IC$_{50}$=1.92 μM, Tables 1 and 2). Besides, removing of a methyl group from piperazinyl moiety (compound I-2) led to lose of selectivity, I-2 inhibits MMP-1, MMP-2, MMP-8, MMP-9, MMP-10, MMP-13, and MMP-14 in IC$_{50}$=1.37+ 6.27 μM. The most active is derivative I-3 with IC$_{50}$=0.96 μM activity on MMP-10. It should be noted, that MMP-3, MMP-7, and MMP-12 are not sensitive to these compounds.

MMP assay: Inhibitors of matrix metalloproteinase enzymes were detected with the use of MMP Inhibitor Fluorimetric Profiling kit (Biornol, USA) accordingly to manufacturer's instructions. MMP activity assays were performed in 96-well plates using the recombinant human MMP-1-10, 12, 13 and 14 catalytic domains and OmniMMP™ fluorogenic substrate SEQ ID No 1: Mca-Pro-Leu-Gly-Leu-Dpa-Ala-Arg-NH$_2$. The test compounds (20 μM) were dissolved in DMSO. The compound NNGH (N-isobutyl-N-(4-methoxyphenylsulfonyl)-glycylhydroxamic acid) was used as a prototypic control inhibitor. The rate of substrate hydrolysis was determined by fluorescence intensity measuring for 10 minutes at 37° C. temperature using a fluorescence plate reader (Tecan infinite M1000, Austria) with excitation at 328 nm and emission at 420 nm. Data analysis was performed using program Graph Pad Prism® 3.0.

TABLE 1

Matrix metalloproteinases inhibition caused by selenopheno[3,2-h]chromenes I-1-I-4 (20 μM)

| Compound | MMP 1 | MMP 2 | MMP 3 | MMP 7 | MMP 8 | MMP 9 | MMP 10 | MMP 12 | MMP 13 | MMP 14 |
|---|---|---|---|---|---|---|---|---|---|---|
| NNGH* (1.3 μM) | 100 | 100 | 100 | 7.2 | 100 | 100 | 100 | 100 | 100 | 100 |
| I-1 | 29 ± 2 | 51 ± 2 | 34 ± 2 | 28 ± 2 | 56 ± 2 | 35 ± 5 | 97 ± 2 | 0 ± 2 | 0 ± 1 | 58 ± 2 |
| I-2 | 94 ± 1 | 98 ± 1 | 31 ± 7 | 20 ± 1 | 100 ± 1 | 100 ± 1 | 99 ± 0 | 5 ± 1 | 98 ± 1 | 98 ± 2 |
| I-3 | 94 ± 2 | 100 ± 1 | 35 ± 5 | 20 ± 3 | 100 ± 1 | 99 ± 1 | 100 ± 1 | 0 ± 2 | 97 ± 4 | 99 ± 4 |
| I-4 | 99 ± 8 | 99 ± 6 | 34 ± 8 | 16 ± 3 | 100 ± 9 | 99 ± 6 | 99 ± 8 | 7 ± 3 | 95 ± 8 | 99 ± 7 |

*N-isobutyl-N-(4-methoxyphenylsulfonyl)-glycylhydroxamic acid

TABLE 2

| Compound | MMP 1 | MMP 2 | MMP 3 | MMP 7 | MMP 8 | MMP 9 | MMP 10 | MMP 12 | MMP 13 | MMP 14 |
|---|---|---|---|---|---|---|---|---|---|---|
| I-1 | >20 | 20 | >20 | >20 | 20 | >20 | 1.92 ± 0.09 | ne | ne | 18 ± 2 |
| I-2 | 5.93 ± 0.54 | 1.57 ± 0.18 | >20 | ne | 1.64 ± 0.25 | 1.48 ± 0.11 | 1.37 ± 0.85 | ne | 6.27 ± 0.65 | 4.35 ± 1.02 |
| I-3 | 6.66 ± 0.85 | 1.13 ± 0.08 | >20 | ne | 1.61 ± 0.14 | 1.06 ± 0.07 | 0.96 ± 0.21 | ne | 4.95 ± 1.05 | 3.88 ± 0.99 |
| I-4 | 5.21 ± 0.62 | 1.86 ± 0.21 | >20 | ne | 1.86 ± 0.22 | 1.92 ± 0.31 | 1.71 ± 0.18 | ne | 4.74 ± 0.95 | 4.04 ± 0.97 |

Matrix metalloproteinases inhibition caused by selenopheno[3,2-h]chromenes I-1-I-4 ($IC_{50}$, µM)

ne—no effect

The invention claimed is:

1. A compound selected from the group consisting of those of Formula I:

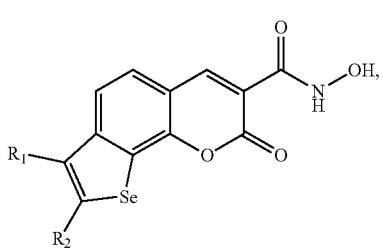

optical isomers thereof, polymorphs thereof, pharmaceutically acceptable acid addition salts thereof, and hydrates and solvates thereof, wherein
$R_1$ represents a halogen atom; and
$R_2$ represents $C_{1-4}$-alkyl N-containing heterocyclyl.

2. The compound according to claim 1, wherein the compound is selected from the group consisting of:

7-Bromo-N-hydroxy-8-((4-methylpiperazin-1-yl)methyl)-2-oxo-2H-selenopheno[3,2-h]chromene-3-carboxamide;

7-Bromo-N-hydroxy-2-oxo-8-((piperazin-1-yl)methyl)-2H-selenopheno[3,2-h]chromene-3-carboxamide;

7-Bromo-N-hydroxy-2-oxo-8-(2-(piperazin-1-yl)ethyl)-2H-selenopheno[3,2-h]chromene-3-carboxamide;

8-((1,4-Diazepan-1-yl)methyl)-7-bromo-N-hydroxy-2-oxo-2H-selenopheno[3,2-h]chromene-3-carboxamide;

and pharmaceutically acceptable enantiomers, diastereomers, racemates, and salts thereof.

3. The compound according to claim 1, wherein the compound has the structure:

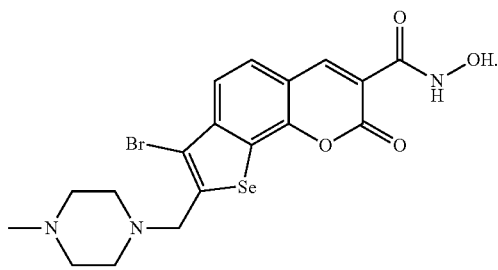 [SMILES: CN1CCN(Cc2[se]c3c(ccc4cc(C(=O)NO)c(=O)oc43)c2Br)CC1]

4. A process for the synthesis of a compound of Formula I:

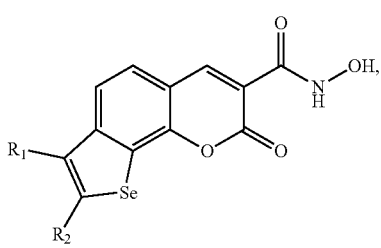

wherein:
R₁ represents Br;
R₂ represents C₁₋₄-alkyl N-containing heterocyclyl;
comprising:
(1) reacting compound 1-4:

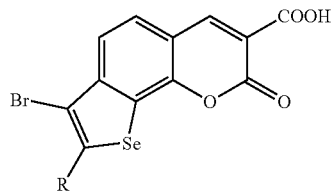

in which R is R₂, with O-(tetrahydro-2H-pyran-2-yl)hydroxylamine, 1-hydroxybenzotriazole and N-(3-dimethylaminopropyl)-N'-ethylcarbodiimide hydrochloride to obtain intermediate 5-8:

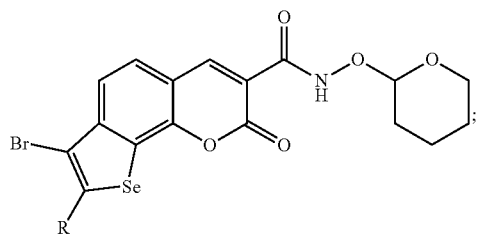

and
(2) reacting intermediate 5-8 with hydrogen chloride to obtain the compound of Formula reaction of a compound of intermediate 5-8.

5. The compound of claim 1, wherein R₁ is F, Cl, Br, or I.

6. The compound of claim 5, wherein R₁ is Br.

7. The compound of claim 6, wherein R₂ is C₁₋₄-alkyl N-containing heterocyclyl, in which the N-heterocyclyl group comprises two nitrogen atoms and is optionally substituted by methyl.

8. The compound of claim 7, wherein R₂ is C₁₋₄-alkyl-piperazinyl or C₁₋₄-alkyl-diazepanyl, in which the piperazinyl group is optionally substituted by methyl.

9. The compound of claim 8, wherein R₂ is (methylpiperazinyl)methyl, piperazinylmethyl, piperazinylethyl, or diazepanylmethyl.

10. The process of claim 4, wherein R₂ is C₁₋₄-alkyl N-containing heterocyclyl, in which the N-heterocyclyl group comprises two nitrogen atoms and is optionally substituted by methyl.

11. The process of claim 10, wherein R₂ is C₁₋₄-alkyl-piperazinyl or C₁₋₄-alkyl-diazepanyl, in which the piperazinyl group is optionally substituted by methyl.

12. The process of claim 11, wherein R₂ is (methylpiperazinyl)methyl, piperazinylmethyl, piperazinylethyl, or diazepanylmethyl.

13. A method of treating a disease, comprising administering to a patient in need thereof a therapeutically effective amount of the compound of claim 1, wherein the disease is atheroma, arthritis, cancer, or tissue ulceration.

14. The method of claim 13, wherein R₁ is F, Cl, Br, or I.

15. The method of claim 14, wherein R₁ is Br.

16. The method of claim 15, wherein R₂ is C₁₋₄-alkyl N-containing heterocyclyl, in which the N-heterocyclyl group comprises two nitrogen atoms and is optionally substituted by methyl.

17. The method of claim 16, wherein R₂ is C₁₋₄-alkyl-piperazinyl or C₁₋₄-alkyl-diazepanyl, in which the piperazinyl group is optionally substituted by methyl.

18. The method of claim 17, wherein R₂ is (methylpiperazinyl)methyl, piperazinylmethyl, piperazinylethyl, or diazepanylmethyl.

19. The method of claim 13, wherein the compound is selected from the group consisting of:
7-Bromo-N-hydroxy-8-((4-methylpiperazin-1-yl)methyl)-2-oxo-2H-selenopheno[3,2-h]chromene-3-carboxamide;
7-Bromo-N-hydroxy-2-oxo-8-((piperazin-1-yl)methyl)-2H-selenopheno[3,2-h]chromene-3-carboxamide;
7-Bromo-N-hydroxy-2-oxo-8-(2-(piperazin-1-yl)ethyl)-2H-selenopheno[3,2-h]chromene-3-carboxamide;
8-((1,4-Diazepan-1-yl)methyl)-7-bromo-N-hydroxy-2-oxo-2H-selenopheno[3,2-h]chromene-3-carboxamide;
and pharmaceutically acceptable enantiomers, diastereomers, racemates, and salts thereof.

20. The method of claim 13, wherein the compound has the structure:

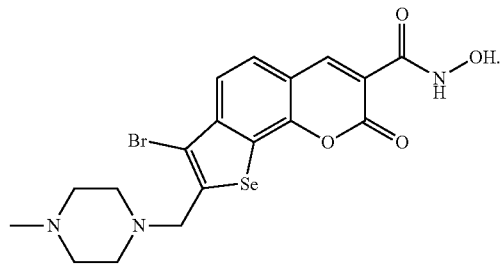 [SMILES: CN1CCN(Cc2[se]c3c(ccc4cc(C(=O)NO)c(=O)oc43)c2Br)CC1]

21. A method of inhibiting angiogenesis, comprising administering to a patient in need thereof a therapeutically effective amount of the compound of claim 1.

22. A method of inhibiting MMP in a cell, comprising contacting the cell with an effective amount of the compound of claim 1.

* * * * *